United States Patent
Nagy et al.

(10) Patent No.: US 6,800,758 B1
(45) Date of Patent: Oct. 5, 2004

(54) PROCESS FOR THE PREPARATION OF A 3 (2H)-PYRIDAZINONE-4- SUBSTITUTED AMINO 5-CHLORO DERIVATIVE

(75) Inventors: Peter Kótay Nagy, Vac (HU); Gyula Simig, Budapest (HU); József Barkóczy, Budapest (HU); Ilona Sztruhár, Budapest (HU); László Balázs, Budapest (HU); Imre Domán, Budapest (HU); Zoltán Greff, Budapest (HU); Zoltán Rátkai, Budapest (HU); Peter Seres, Budapest (HU); Támas Karancsi, Budapest (HU)

(73) Assignee: Egis Gyogyszergyar Rt., Budapest (HU)

( * ) Notice: Subject to any disclaimer, the term of this patent is extended or adjusted under 35 U.S.C. 154(b) by 0 days.

(21) Appl. No.: 09/701,732

(22) PCT Filed: Jun. 5, 1998

(86) PCT No.: PCT/HU98/00054

§ 371 (c)(1),
(2), (4) Date: Feb. 9, 2001

(87) PCT Pub. No.: WO99/64402

PCT Pub. Date: Dec. 10, 1995

(51) Int. Cl.[7] .............................................. C07D 237/14
(52) U.S. Cl. ...................................... 544/241; 544/224
(58) Field of Search ......................................... 544/241

(56) References Cited

U.S. PATENT DOCUMENTS

| 4,532,239 A | 7/1985 | Raabe et al. ................. 514/247 |
| 5,395,934 A | 3/1995 | Matyus et al. .............. 544/241 |

FOREIGN PATENT DOCUMENTS

| EP | 0 054 946 | 6/1982 |
| GB | 2 262 526 | 6/1993 |

*Primary Examiner*—Emily Bernhardt
(74) *Attorney, Agent, or Firm*—Smith, Gambrell & Russell

(57) ABSTRACT

The invention relates to novel processes for the preparation of 5-chloro-4-{3-[N-[2-(3,4-dimethoxyphenyl)-ethyl]-N-methylamino]-propylamino-3(2H) pyridazinone of formula (I) and the pharmaceutically acceptable acid addition salts thereof. An important feature of the invention is using 3,4,5-trichloropyridazone as starting substance of the synthesis.

5 Claims, No Drawings

PROCESS FOR THE PREPARATION OF A 3 (2H)-PYRIDAZINONE-4- SUBSTITUTED AMINO 5-CHLORO DERIVATIVE

The invention relates to a process for the preparation of 5-chloro-4-{3-[N-[2-(3,4-dimethoxyphenyl)-ethyl]-N-methyl-amino]-propylamino}-3(2H)-pyridazinone of the formula (I).

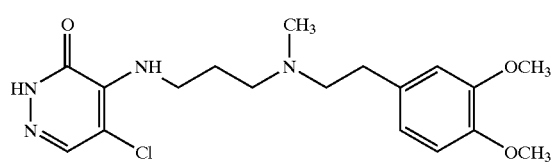
(I)

The British patent specification No. 2 262 526 provides new 3(2H)-pyridazinone-4-substituted amino-5-halo derivatives which possess valuable antiarrhythmic properties and prevent ventricular and auricular fibrillations. The 5-chloro-4-{3-[N-[2-(3,4-dimethoxyphenyl)-ethyl]-N-methyl-amino]-propylamino}-3(2H)-pyridazinone of formula (I) is described in the above-mentioned British patent specification.

According to the British patent specification No. 2 262 526 the compound of formula (I) is prepared by reacting 4,5-di-chloro-3(2H)-pyridazinone of formula (XI)

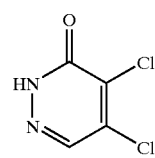
(XI)

with the amine of formula (X).

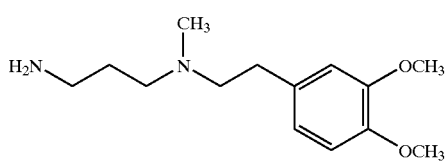
(X)

The drawback of the process resides in the fact that a mixture of the desired compound of formula (I) and the regioisomer thereof of formula (IA)

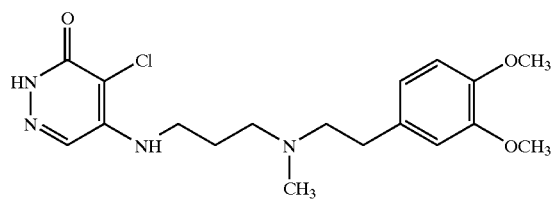
(IA)

is obtained, wherein the main component is the undesired isomer of formula (IA), while the desired compound of formula (I) is present only as a side-product, in an amount of a few %. Only by expensive and cumbersome column chromatography can the compound of formula (I) be separated and isolated in a pure state from the thus-obtained mixture. A further disadvantage of the method is that a considerable (2.5–3-fold) molar excess of the expensive amino component of formula (X) obtained in a multi-step reaction is applied, which renders the method less economical.

The present invention aims at providing a more regioselective method for the preparation of 5-chloro-4-{3-[N-[2-(3,4-dimethoxyphenyl)-ethyl]-N-methylamino]-propyl-amino}-3(2H)-pyridazinone of the formula (I), which is devoid of the drawbacks of the hitherto known processes.

It has been found that the above aim can be achieved by producing the 5-chloro-4-{3-[N-[2-(3,4-dimethoxyphenyl)-ethyl]-N-methylamino]-propylamino}-3(2H)-pyridazinone of formula (I) and pharmaceutically acceptable acid addition salts thereof according to the method of the invention, which comprises a$_1$) reacting a compound of the general formula (II),

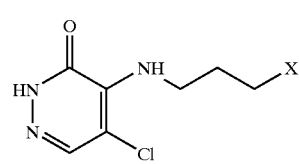
(II)

wherein X stands for a leaving group, with N-methyl-homoveratryl amine of the formula (VI);

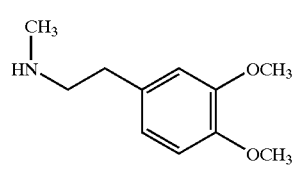
(VI)

or a$_2$) reacting a compound of the general formula (III),

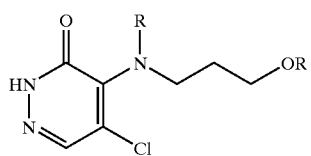
(III)

wherein R stands for lower alkanoyl, aroyl or aryl-(lower alkanoyl), with an agent containing a leaving group of the formula X and reacting the thus-obtained compound of the general formula (II) with the compound of formula (VI); or a$_3$) reacting 4-(3-hydroxypropylamino)-3,5-dichloro-pyridazine of the formula (IV)

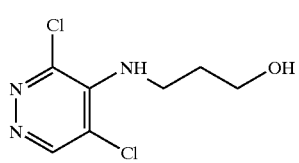
(IV)

with an agent suitable for introducing a group of the formula R, reacting the thus-obtained compound of general formula (III) with an agent containing a leaving group of the formula X and reacting the thus-obtained compound of general formula (II) with the compound of formula (VI); or a₄) reacting 3,4,5-trichloropyridazine of the formula (V)

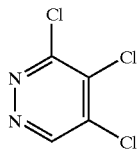

(V)

with 3-amino-1-propanol, reacting the thus-obtained compound of formula (IV) with an agent suitable for introducing a group of the formula R, reacting the thus-obtained compound of general formula (III) with an agent containing a leaving group of the formula X and reacting the thus-obtained compound of general formula (II) with a compound of the formula (VI); or b₁) removing the group of the formula R (wherein R is as stated above) from a compound of general formula (IX);

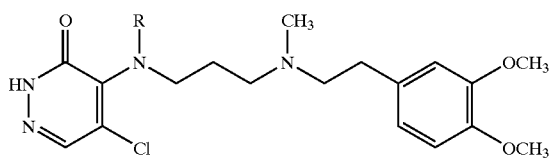

(IX)

or b₂) reacting the compound of formula (VIII)

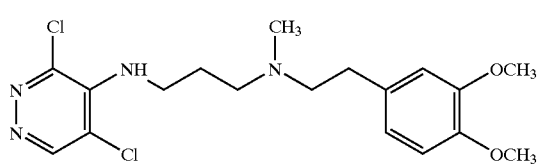

(VIII)

with an agent suitable for introducing a group of the formula R and removing the group of formula R from the thus-obtained compound of general formula (IX); or b₃) reacting a compound of the general formula (VII),

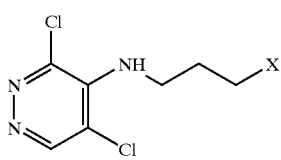

(VII)

wherein X is as stated above, with a compound of the formula (VI), reacting the thus-obtained compound of formula (VIII) with an agent suitable for introducing a group of the formula R, and removing the group of the formula R from the thus-obtained compound of general formula (IX); or b₄) reacting the compound of formula (IV) with an agent containing a leaving group of the formula X, reacting the thus-obtained compound of general formula (VII) with the compound of formula (VI), reacting the thus-obtained compound of general formula (VIII) with an agent suitable for introducing a group of the formula R and removing the group of the formula R from the thus-obtained compound of general formula (IX);

and, if desired, converting the thus-obtained compound of formula (I) into an acid addition salt thereof.

The invention is based on the discovery that the regioselectivity of the reaction can be improved considerably when using 3,4,5-trichloropyridazine of the formula (V) as starting substance. When reacting the compound of formula (V) with 3-amino-1-propanol an approximately 1:1 mixture of the desired compound of formula (IV) and the regioisomer thereof of formula (IVA)

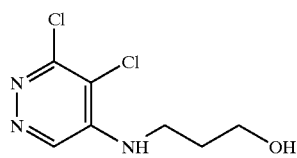

(IVA)

is obtained. A further advantage of the application of the compound of formula (V) as starting substance resides in the fact that the isomers of formulae (IV) and (IVA) can readily be separated by crystallization, and thus the expensive column chromatography cumbersome on an industrial scale can be eliminated. A further advantage of the process according to the invention is that the regioisomers are separated at the beginning of the synthesis, when the first intermediate is formed, so the further reaction steps and the closing step are carried out with the application of only one regioisomer. Thus the desired product can be separated from the reaction mixture with a reduced loss and in a higher purity compared to the hitherto known processes. It was not aforeseen that the regioisomers of formulae (IV) and (IVA) can be separated so simply, by crystallization, and converted to the compounds of general formulae (II) and (III) with such a high yield.

In the first step of variant a) according to the invention 3,4,5-trichloropyridazine of the formula (V) is reacted with 3-amino-1-propanol. The reaction is carried out in an organic solvent. As reaction medium preferably lower alkanols (such as methanol, ethanol, n-propanol, preferably ethanol) or dipolar aprotic solvents (such as acetonitrile or dimethylformamide) are used. The reaction is carried out in the presence of an acid binding agent. For this purpose inorganic acid binding agents (e.g. alkali carbonates, such as sodium carbonate or potassium carbonate, alkali hydrogen carbonates, such as sodium hydrogen carbonate or potassium hydrogen carbonate), or organic acid binding agents (e.g. amines, such as triethylamine or diethyl isopropyl amine) can be used. According to a preferable embodiment of the process according to the present invention the excess of 3-amino-1-propanol used as reactant may serve as solvent. The reaction can be performed at a temperature between 50° C. and 100° C., preferably at the boiling point of the reaction mixture.

When the reaction has been accomplished the reaction mixture is preferably worked up by removing the solvent and treating the residue with distilled water or with a 5 to 15% sodium chloride solution. Thus the two isomers can readily be separated, as the precipitate rich in the undesired isomer of the formula (IVA) can be isolated easily, by filtration, from the aqueous solution rich in the desired isomer of the formula (IV). If desired, both isomers can be subjected to further purification. The isomer of formula (IVA) can be purified by re-crystallization from an alcohol, while the compound of formula (IV) can be purified by extraction carried out with an organic solvent (e.g. ethyl acetate or halogenated hydrocarbons, such as dichloroethane or chloroform) followed by drying and evaporating the extract and re-crystallizing the residue from diethyl ether.

In the second reaction step of variant a) the thus-obtained compound of formula (IV) is reacted with an agent suitable for introducing a group of the formula R, wherein R is a lower alkanoyl (e.g acetyl, propionyl or butyryl), aroyl (e.g. benzoyl optionally carrying a substituent selected from the group consisting of halogen, alkoxy and trifluoro-methyl) or aryl-(lower alkanoyl) (e.g. phenylacetyl). Compounds of the general formula (III) containing an acetyl group in the place of R can be prepared and used advantageously in the synthesis.

The starting compound of formula (IV) applied for the second step of the synthesis may be either purified or unpurified. Surprisingly it has been found that when the compound of the formula (IV) is unpurified, the compound of general formula (III) is obtained in at least such a high purity and good yield than when starting from a purified compound of the formula (IV). If a compound of the general formula (III) containing acetyl in the place of R is prepared, the compound of formula (IV) is reacted with acetic acid, in the presence of an excess of sodium acetate. As reaction medium preferably glacial acetic acid is used and the sodium acetate is applied in a 2.5 to 3-fold molar excess. The reaction may be carried out at a temperature between 80° C. and 120° C., it is performed preferably at a temperature of about 100° C. The reaction mixture can be worked up by extraction carried out with an organic solvent (preferably dichloromethane) followed by drying and evaporating the organic phase. The product is purified by recrystallization from an alkanol (preferably methanol).

The compound of formula (III) obtained in the third reaction step of variant a) is reacted with an agent containing a leaving group of the formula X, wherein X represents preferably a halogen atom (e.g. chlorine or bromine) or an alkylsulfonyloxy (such as benzenesulfonyl-oxy, p-tolylsulfonyloxy or p-bromophenylsulfonyloxy) group.

It is preferable to carry out the reaction via an intermediate of the general formula (II), wherein X stands for bromine. In this case the compound of general formula (III) is reacted with an aqueous hydrogen bromide solution. It is preferable to use a 48% aqueous hydrogen bromide solution. Thus the group of formula R can be removed from the amino and hydroxy groups in excellent yields an in a single reaction step, and 4-(3-bromopropylamino)-5-chloro-3(2H)-pyridazinone of the formula (II) is obtained. The reaction is carried out at a temperature between 80° C. and 110° C., preferably at about 98° C. The reaction mixture can be worked up readily. The separated product is isolated by filtration or centrifugation and optionally crystallized from an alcohol. The compound of general formula (II) containing a bromine atom in the place of X is a highly preferable intermediate, because the bromine atom is a leaving group easy to be split off.

In the next reaction step of variant a) the compound of general formula (II) is reacted with N-methyl-N-[2-(3,4-dimethylphenyl)-ethyl]-amine (N-methyl-homoveratrylamine). The reaction is carried out in a solvent, in the presence of an acid binding agent. As reaction medium preferably dipolar aprotic solvents (such as acetone, acetonitrile or dimethyl-formamide) may be used. As acid binding agent inorganic compounds (e.g. alkali carbonates, such as sodium carbonate or potassium carbonate, or alkali hydrogen carbonates, such as sodium hydrogen carbonate or potassium hydrogen carbonate) or organic compounds (e.g. triethyl-amine or dipropylethylamine) may be used. The reaction is carried out at a temperature between 40° C. and the boiling point of the reaction mixture. One can also proceed by applying excess amine of the formula (VI) which may serve as acid binding agent.

The reaction mixture can be worked up by known methods, e.g it is evaporated and the residue is poured into water, extracted with an organic solvent (such as dichloromethane or ethyl acetate), the organic extract is filtered, dried and purified by crystallization.

In the first step of variant b) of the process according to the invention the compound of formula (IV) is reacted with an agent containing a leaving group of the formula X. When preparing compounds of the general formula (VII) containing bromine or chlorine in the place of X the compound of formula (IV) is reacted with thionyl bromide or phosphorus oxybromide, or thionyl chloride or phosphorus oxychloride respectively. The reaction is carried out at a temperature between −10° C. and 100° C., in an inert organic solvent. As solvent halogenated hydrocarbons (such as dichloromethane, dichloroethane, chloroform, trichloroethylene, chloro-benzene or carbon tetrachloride), dipolar aprotic solvents (such as acetonitrile) or aromatic solvents (such as benzene or toluene) may be used. The compound of general formula (VII), wherein X stands for bromine, can be prepared from the compound of formula (IV) with aqueous hydrogen bromide in organic acids (e.g. acetic or formic acid), at a temperature between 20° C. and 150° C. as well.

The compounds of general formula (VII), wherein X stands for alkylsulfonyloxy or arylsulfonyloxy, can be prepared by reacting the compound of formula (IV) with an appropriate sulfonic chloride in an inert solvent, in the presence of an acid binding agent, at a temperature between −20° C. and 60° C. As reaction medium halogenated hydrocarbons (such as trichloromethane, dichloroethane, chloroform, trichloroethylene, chlorobenzene or carbon tetrachloride) or aromatic hydrocarbons (e.g. benzene or toluene) may be applied. As acid binding agent organic bases (e.g. triethylamine or pyridine) can be used.

In the next reaction step of variant b) the thus-obtained compound of general formula (VII) is reacted with an amine of the formula (VI). The reaction is preferably carried out in a dipolar aprotic solvent (such as acetone, aceco-nitrile, dimethylformamide) in the presence of an acid binding agent. As acid binding agent inorganic compounds (such as potassium carbonate or potassium hydrogen carbonate) or organic compounds (such as triethylamine) can be used. An excess of the amine of the formula (VI) may also serve as acid binding agent. The reaction is carried out at a temperature between 10° C. and the boiling point of the reaction mixture. The reaction mixture can be worked up by known methods, e.g. the solvent is removed, the residue is poured onto water, extracted with an organic solvent (such as dichloromethane or diethyl acetate) and the extract is filtered and dried.

The thus-obtained compound of general formula (VIII) is then reacted with an agent suitable for introducing the group of formula R. The reaction is carried out as specified above in connection with the conversion of the compound of formula (IV) into the compound of formula (III). Preferably compounds of the general formula (IX) containing an acetyl group in the place of R are prepared. For this purpose it is preferable to carry out the reaction of the compound of formula (VIII) in glacial acetic acid, in the presence of anhydrous sodium acetate applied in a 1 to 5-fold molar excess, at a temperature between 40° C. and 140° C., preferably between 80° C. and 120° C.

In the last reaction step of variant b) the group of formula R is removed from the compound of general formula (IX). The reaction is preferably carried out with hydrogen bromide, particularly with 48% aqueous hydrogen bromide.

The thus-obtained compound of general formula (I) is optionally converted into a pharmaceutically acceptable acid addition salt. The salt formation is carried out by methods known per se, with acids generally used in the pharmacological industry. Both inorganic acids (such as hydrogen chloride, hydrogen bromide, phosphoric acid, sulfuric acid etc.) and organic acids (such as maleic, fumaric, citric, malic, lactic, succinic acid etc.) may be applied. It is preferable to prepare the acid addition salt of the compound of formula (I) formed with hydrogen chloride or fumaric acid.

The compound of formula (V) can be prepared by reacting 4,5-dichloro-3(2H)-pyridazinone with phosphorous oxychloride [T. Kuraishi: Pharm. Bull. (Tokyo) 4, 497 (1956)].

The advantages of the process according to the invention compared to the hitherto known processes are as follows:
- the reaction is significantly more regioselective than the known processes,
- the desired isomer can be separated from the obtained regioisomer by a simple crystallization, thus the complicated column chromatography cumbersome on an industrial scale can be eliminated,
- the regioisomers are separated at an early stage of the synthesis, consequently only one regioisomer is used in the further steps of the process,
- the reaction steps can be carried out in high yields (e.g. the preparation of the compounds of the formulae (II) and (III)), the end-product of the formula (I) is obtained in a high yield and with high purity.

The invention is further illustrated by the following Examples of non-limiting character:

EXAMPLE 1

4-(3-hydroxypropylamino)-3,5-dichloropyridazine (IV) and 5-(3-hydroxypropylamino-3.4-dichloropyridazine (IVA)

47.93 g (0.261 mole) of 3,4,5-trichloro-pyridazine are dissolved in ethanol and 49.7 ml (r=0.982 g/cm$^3$, 0.65 mole) of 3-amino-1-propanol are added to it under stirring. The solution is heated to boiling, boiled for 30 minutes and a sample is taken for TLC (eluent: a 10:10:0.5 mixture of ethyl acetate:acetone:triethylamine, $R_f$ values: (XI)=0.90, (IV)= 0.48, (IVA)=0.32, contamination of unknown stucture= 0.75). The reaction takes place generally within 30 minutes and 1 hour, the whole amount of the starting substance is used up. The reaction mixture is then evaporated, 13 g of sodium chloride are dissolved in distilled water and the thus-obtained solution is added to the evaporated mixture under stirring. The reaction mixture is allowed to stand in a refrigerator overnight at 5° C. The separated crystals are washed with 10 to 12 ml of cold distilled water and the precipitate is dried. Thus 27.7 g (47.7%) of crude product (IVA) are obtained. M.p.: 150–153° C. After recrystallization from methanol the melting point rises to 157–158° C. The physical characteristics will be specified later.

The aqueous mother liquor is extracted 5 times with 200 cm$^3$ each of ethyl acetate, dried over hot magnesium sulfate, filtered on activated carbon and evaporated to dry. The bulk of the residual crude product is the compound of formula (IV).

Yield of the crude product: 28.02 g (48.32%), according to HPLC analysis it contains 7 to 8% of (IVA) and 1 to 2% of contamination of unknown structure. The crude product is purified by recrystallization from cold diethyl ether in the following way: 300 ml of diethyl ether are added to it in 5 portions and the oily product is stirred at room temperature. The ether solution is decanted on every occasion and fresh ether is used. The ether solutions are combined, evaporated to a volume of 100 ml and the separated crystals are filtered off. Thus 15.6 g (26%) of compound of the formula (IV) are obtained. M.p.: 65–66° C. According to MPLC analysis carried out after purification (IVA) <3.0% and (IV)>97%. For the elaboration of the HPLC method small amounts of standards have been prepared by column chromatography. HPLC method:

Column: Ultrasphere SI 3 mm. 75 cm×4.6 mm.
Eluent: cyclohexane:ethyl acetate (1:1).
Flow rate: 1.0 ml/min.
Detection: UV 254 nm.
Injected volume: 20 ml (0.8% dilution).
Retention times: 5.13 for compound (IV) and 13.46 minutes for compound (IVA).

The Physico-chemical Characteristics of 4-(3-hydroxypropyl-amino)-3,5-dichloropyridazine (IV)

M.p.: 65–66° C.
TLC: ethyl acetate:triethylamine=20:0.5
$R_f$=0.36

| Analysis for the formula $C_7H_9Cl_2NO_3$ (222.08): | | | |
|---|---|---|---|
| C | H | Cl | N |
| Calculated: | | | |
| 37.86% | 4.09% | 31.93% | 18.92% |
| Found: | | | |
| 37.62 | 4.12% | 31.71% | 18.67% |

IR (KRr) ν cm$^{-1}$:
3249, 2947, 1591, 1454, 1390, 1353, 1212, 1177, 1124, 1075, 1037, 908, 683, 522, 460.

$^1$H-NMR (DMSO): δ 8.70 [s, (1H) pyridazine C-6 ], 6.8 [t, (1H) 4-NH], 4.7 [t, (1H) OH], 3.74 [qa, (2H) N—CH$_2$], 3.5 [qa, (2H) CH$_2$—O—] 1.73 [m, (2H) C—CH$_2$—C].

$^{13}$CNMR (DMSO) δ ppm: 150.8, 116.0, 140.1, 114.7 (pyridazine carbon atoms), (60 C—OH), (43.6 NH—C), (31.9 C—CH$_2$—C).

Physico-chemical Characteristics of the 5-(3-hydroxypropyl-amino)-3.4-dichloropyridazine (IVA)

M.p.: 157–158° C.
TLC: ethyl acetate:triethylamine=20:0.5
$R_f$=0.16

| Analysis for the formula $C_7H_9Cl_2N_3O$ (222.08): | | | |
|---|---|---|---|
| C | H | Cl | N |
| Calculated: | | | |
| 37.86% | 4.09% | 31.93% | 18.92% |
| Found: | | | |
| 37.68 | 4.11% | 31.77% | 18.73% |

-continued

Analysis for the formula $C_7H_9Cl_2N_3O$ (222.08):

| C | H | Cl | N |
|---|---|----|---|

IR (KBr) ν cm$^{-1}$:

3269, 2935, 1568, 1334, 1283, 1224, 1139, 1070, 1043, 861, 830, 795, 661, 540, 514.

$^1$H-NMR (DMSO): δ ppm: 8.73 [s,(1H) pyridazine C-6], 7.59 [t,(1H) 5-NH], 4.66 [t,(1H) OH], 3.4–3.6 [m,(4H) CH$_2$-X X=heteroatom], 1.73 [m,(2H) C—CH$_2$C].

The stereoscopic vicinity of the NH proton at position 5 and the pyridazine proton at position 6 has been proved by a DNOE experiment.

$^{13}$CNMR (DMSO) δ ppm: 152.1, 143.7, 137.2, 114.4 (pyridazine carbon atoms), (58.4 C—OH), (39.9 C—NH), (31.4 C—CH$_2$—C).

EXAMPLE 2

Preparation of 4-N-acetyl-4-N-(3-acetoxy-propyl)-5-chloro-3(2H)-pyridazinone (III)

Method A

A mixture of 3 g (13.5 mmoles) of 4-(3-hydroxypropylamino)-3,5-dichloropyridazine (IV) and 3 g (36.5 mmoles) of anhydrous sodium acetate is suspended in 30 cm$^3$ of glacial acetic acid, and the mixture is boiled for 3 hours (TLC ethyl acetate:aceton:triethylamine==10:10:0.5). The starting substance (R$_f$=0.48) is used up. The reaction mixture is then cooled, 100 cm$^3$ of distilled water are added to it and the mixture is extracted 3 times with 50 cm$^3$ each of dichloromethane. The organic phases are combined, dried over magnesium sulfate, filtered with activated coal and evaporated. The crude oily residue is dissolved in 5 cm$^3$ of hot methanol. Upon cooling 4-N-acetyl-4-N-(3-acetoxypropyl)-5-chloro-3(2H)-pyridazinone (III) begins to separate. The separated crystals are filtered and washed successively with cold methanol and ether. Yield: 2.0 9 (51.6%).

Method B

A mixture of 28 g (0.12 mole) of crude compound of the formula (IV) and 28 g (0.34 mole) of anhydrous sodium acetate is suspended in 280 cm$^3$ of glacial acetic acid. The mixture is heated to boiling and the reaction is followed as specified above. The mixture is then cooled, the sodium acetate is filtered off and washed with glacial acetic acid. The mother liquor is evaporated in vacuo. For the complete removal of the acetic acid 2×50 cm$^3$ of toluene are added to the mixture and it is evaporated again. The residue is then dissolved in 100 cm$^3$ of distilled water, the aqueous mother liquor is extracted 3 times with 100 cm$^3$ each of dichloromethane, dried over magnesium sulfate, filtered over activated carbon and evaporated. The residual crude product (29–30 g) is dissolved in 15–20 cm$^3$ of hot methanol, clarified by activated carbon and filtered while hot. The product separates upon cooling. It is filtered and washed successively with cold methanol and cold ether. Yield: 16–20 g (45–50%).

The physical and chemical characteristics of the compound of formula (III) prepared according to any of methods A and B have been found identical.

Physical and Chemical Characteristics of the 4-N-acetyl-4N-(3-acetoxypropyl)-S-chloro-3(2H)-pyridazinone (III)

M.p.: 108–110° C.

TLC: acetonitrile:methanol=9:1 R$_f$=0.75

Analysis for the formula $C_{11}H_{14}ClN_3O_4$:

| C | H | Cl | N |
|---|---|----|---|
| Calculated: | | | |
| 45.92% | 4.91% | 12.32% | 14.61% |
| Found: | | | |
| 45.63% | 5.01 | 12.36% | 14.40% |

IR (KBr) ν cm$^{-1}$:

3400–2800 [pyridazinone ring (NH—CO)], 1729, 1676 (amides), 1593, 1445, 1406, 1362, 1321, 1256, 1205, 1172, 1128, 1099, 1083, 1032, 971, 945, 888, 845, 831, 777, 741, 637, 610, 569, 448, 427.

$^1$H-NMR (400 MHz, CDCl$_3$) δ ppm: 12.8 [s, (1H) pyridazinone-NH], 7.97 [s, (1H) pyridazinone C-6H], 4.12 [t, (2H) J=6.5 Hz, —CH$_2$O], {3.8 [m, (1H) and 3.7 [m, (1H), —N—CH$_2$}, 2.03 [s, (3H), CH$_3$], 1.97 [s, (3H) CH$_3$], 1.89 [m, (2H), C—CH$_2$—C].

$^{13}$CNMR (400 MHz CDCl$_3$) δ ppm: 171.07, 169.68, (acetyl-carbonyl carbon atoms), 159.87 (CO-pyridazinone), 138.2, 138.4, 139.9 (carbon atoms of the pyridazinone ring), 62.0 CH$_2$—O), 44.2 (CH$_2$—N) , 27.4 (CH$_2$), 21.7 and 20.9 (CH$_3$ carbon atoms).

The advantage of method B resides in the elimination of the loss of substance during the recrystallization from diethyl ether.

EXAMPLE 3

4-(3-bromopropylamino)-5-chloro-3(2H)-2pyridazinone (II)

30.5 g (0.106 mole) of 4-N-acetyl-4-N-(3-acetoxypropyl)-5-chloro-3(2H)-pyridazinone (III) are suspended in 136 cm$^3$ of 48% aqueous hydrogen bromide solution in a flask that may be closed by a Du Pont screw-cap. The reaction mixture is kept at a temperature between 96° C. and 98° C. for 24 hours under stirring [TLC ethyl acetate:acetone:triethylamine=10:10:0.5 (III) R$_f$=0.73]. During that time the starting substance is used up. The reaction mixture is then cooled, the separated crystals are filtered and washed with cold dichloromethane. Yield: 27.3 g (95%). The crude product is recrystallized from 100 to 110 cm$^3$ of isopropanol. Yield: 20.2 g (73%).

Physical and Chemical Characteristics of the 4-(3-bromo-propylamino)-5-chloro-3(2H)-pyridazinone M.p.: 116–118° C.

TLC: ethyl acetate-acetone-triethylamine==10:10:0.5 R$_f$=0.73

Analysis for the formula $C_7H_9BrClN_3O_4$ (266.53):

| C | H | Cl | N |
|---|---|----|---|
| Calculated: | | | |
| 31.55% | 3.40% | 13.30% | 15.77% |
| Found: | | | |
| 31.74% | 3.45 | 13.15% | 15.70% |

-continued

Analysis for the formula C₇H₉BrClN₃O₄ (266.53):

| C | H | Cl | N |
|---|---|----|---|

IR (KBr) ν cm⁻¹:

3183, 2800, 2400, 1545, 1423, 1374, 1324, 1269, 1239, 1214, 1163, 1107, 1037, 936, 819, 750, 572.

¹H-NMR (DMSO) δ ppm: 12.45 [s, (1H) NH-pyridazine], 7.65 [s, (1H) -pyridazine], 6.4 [s, (1H) 4NH]), 3.78 [t, (2H), N—CH₂], 3.58 [t, (2H), Br—CH₂], 2.13 [qa, (2H), CH₂].

¹³CNMR (DMSO) δ ppm: 156.93 (Co-pyridazinone), 139.8, 105.9 (pyridazinone ring carbon atoms), 34.16 (C—NH), 41.88 (C—Br), 31.95 (CH₂).

EXAMPLE 4

5-chloro-4-{3-[N-[2-(3.4-dimethoxyphenyl)-ethyl]-N-methyl-amino]-propylamino}-3(2H)-pyridazinone (I)

A mixture of 10.66 g (0.04 mole) of 4-(3-bromopropylamino)-5-chloro-3(2H)-pyridazinone (II), 10.0 g (0.05 mole) of N-methyl-homoveratryl amine (VI) and 8 g of potassium hydrogen carbonate is suspended in 80 cm³ of acetone. The reaction mixture is refluxed for 8 to 12 hours. The reaction is followed by TLC (eluent: ethyl acetate: acetone:triethylamine==10:10:0.5 (II R$_f$=0.76), (VI R$_f$=0.14), (I R$_f$=0.47)). The mixture is filtered while hot, washed with acetone and the mother liquor is evaporated in vacuo. To the residue 50 cm³ of ethyl acetate are added. The possibly separated inorganic substance is filtered off and the filtrate is evaporated again. The residual viscous, oily product (14 to 15 g) is triturated twice with 50 cm³ of hot water in order to remove the unreacted starting substance of the formula (VI). The warm aqueous solution is decanted. The oily residue is dissolved in methanol and dried over magnesium sulfate. Upon adding a small amount of diisopropyl ether and cooling the mixture white porous substance separates. Thus 9 g (59.0%) of crude product are obtained. M.p.: 89–90° C. After recrystallization from diisopropyl ether 7.0 g (46.0%) of the title compound are obtained.

Physical and Chemical Characteristics of the 5-chloro-4-{3-[N-[2-(3.4-dimethoxyphenyl)-ethyl]-N-methylamino]-propyl-amino}-3(2H)-pyridazinone M.p.: 90–92° C.

TLC: ethyl acetate-acetone-triethylamine==10:10:0.5

R$_f$=0.45

Analysis for the formula C₁₈H₂₅ClN₄O₃ (380.88):

| C | H | Cl | N |
|---|---|----|---|
| Calculated: | | | |
| 56.76% | 6.62% | 9.31% | 14.71% |
| Found: | | | |
| 56.46% | 6.68 | 9.26% | 14.85% |

-continued

Analysis for the formula C₁₈H₂₅ClN₄O₃ (380.88):

| C | H | Cl | N |
|---|---|----|---|

IR (KBr) ν cm⁻¹:

3290, 3111, 2940, 2860, 2830, 2780, 2700, 1640, 1610, 1570, 1520, 1445, 1350, 1260, 1240, 1140, 1100, 950, 900, 800, 600.

¹H-NMR (200 MHz, CDCl₃) δ ppm: 1.67 [s, (1H) pyridazinone-NH], 7.52 [s, (1H) pyridazinone-CH], 6.75 [m, (3H), Ar—H], 6.62 [t, (1H), NH], 3.84 and 3.86 [s, (6H), CH₃O], 3.85 [m, (2H), propyl-CH₂], 2.72 and 2.65 [m, (4H) ethyl-CH₂], 2.56 [m, (2H), propyl-CH₂], 2.33 [s, (3H), N—CH₃], 1.80 [m, (2H), propyl-CH₂].

¹³CNMR (200 MHz CDCl₃) δ ppm: 157.69 (pyridazinone C3), 148.46, 146.94, 132.64, 120.20, 111.73, 110.93 (CH₃O-phenyl-aromatic carbon atoms), 140.41 (pyridazinone C6), 139.85 (pyridazinone C5), 106.8 (pyridazinone C4), 59.43 (C1-propyl), 55.54 and 55.49 (O—CH₃), 54.83 (C2-ethyl), 42.82 (N—CH₃), 41.67 (C3-propyl), 32.87 (CH₂—Ar), 27.66 (C2-propyl).

EXAMPLE 5

Preparation of the Starting Substance 200 g of commercially available 4,5-dichloro-3(2H)-pyridazinone are refluxed in 1500 cm³ of phosphorus oxychloride for 5 hours. Then the excess of phosphorus oxychloride is distilled off in vacuo. The residue is poured onto icy water, the crystalline product is filtered and dried. Yield: 200 g (89%) of 3,4,5-trichloro-pyridazine. M.p.: 58–60° C.

What we claim is:

1. A process for the preparation of 5-chloro4-{3-[n-[2-(3,4-dimethoxyphenyl)-ethyl]-N-methylamino]-propylamino}-3(2H)-pyridazinone of the formula (I)

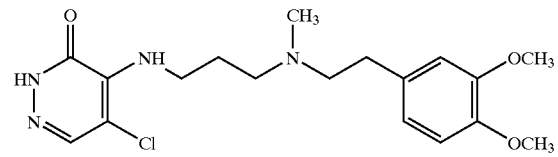

which comprises a1) reacting, in a dipolar aprotic solvent in the presence of an acid binding agent, a compound of the general formula (II),

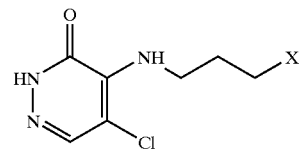

wherein X stands for a leaving group, with N-methyl-homoveratryl amine of the formula (VI);

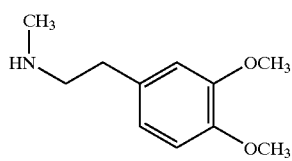

and, if desired, converting the thus obtained compound of formula (I) into an acid addition salt thereof.

2. A process as claimed in claim 1, wherein said solvent is acetone, acetonitrile, or dimethylformamide and said acid binding agent is an alkali carbonate, an alkali hydrogen carbonate or an amine.

3. A process as claimed in claim 2, wherein the amine is triethylamine or an excess of the reagent of formula (VI).

4. A compound of the general formula (II),

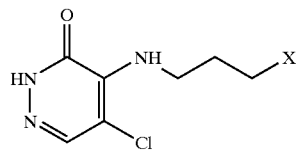

wherein X stands for a leaving group.

5. A compound of the general formula (II) according to claim 4, wherein X stands for bromine.

* * * * *